(12) United States Patent
Kamimura et al.

(10) Patent No.: US 8,993,814 B2
(45) Date of Patent: Mar. 31, 2015

(54) METHOD FOR PRODUCING ALCOHOL COMPOUND

(75) Inventors: Akio Kamimura, Yamaguchi (JP); Kouji Kaiso, Yamaguchi (JP); Tsunemi Sugimoto, Yamaguchi (JP)

(73) Assignee: Yamaguchi University (JP)

( * ) Notice: Subject to any disclaimer, the term of this patent is extended or adjusted under 35 U.S.C. 154(b) by 249 days.

(21) Appl. No.: 13/389,059

(22) PCT Filed: Aug. 2, 2010

(86) PCT No.: PCT/JP2010/062995
§ 371 (c)(1),
(2), (4) Date: Mar. 1, 2012

(87) PCT Pub. No.: WO2011/016409
PCT Pub. Date: Feb. 10, 2011

(65) Prior Publication Data
US 2012/0157707 A1   Jun. 21, 2012

(30) Foreign Application Priority Data

Aug. 5, 2009   (JP) .................................. 2009-182525

(51) Int. Cl.
*C07C 27/00*   (2006.01)
*C07C 29/128*   (2006.01)

(52) U.S. Cl.
CPC .................................... *C07C 29/128* (2013.01)
USPC ....................................................... 568/876

(58) Field of Classification Search
USPC ....................................................... 568/876
See application file for complete search history.

(56) References Cited

U.S. PATENT DOCUMENTS

2004/0202681 A1*   10/2004   Pejaver et al. ................ 424/400

FOREIGN PATENT DOCUMENTS

| EP | 1 566 375 A1 | 8/2005 |
|---|---|---|
| EP | 1 980 551 A1 | 10/2008 |
| JP | 11-292831 | 10/1999 |
| JP | 11-343338 | 12/1999 |
| JP | 2000-086583 | 3/2000 |
| JP | 2002-148253 | 5/2002 |
| JP | 2003-096032 | 4/2003 |
| JP | 2005-232170 | * 9/2005 |
| WO | 2007/088756 A1 | 8/2007 |
| WO | 2008/096568 | 8/2008 |

OTHER PUBLICATIONS

Extended European Search Report which issued in connection with corresponding European Application No. 10806408.0 on Jun. 11, 2014.

* cited by examiner

*Primary Examiner* — Yong Chu
*Assistant Examiner* — Sonya Wright
(74) *Attorney, Agent, or Firm* — Clark Hill PLC

(57) ABSTRACT

Provided is a method for producing an alcohol compound, which enables the alcohol compound to be obtained at a high yield from an amide compound or amine compound. The method for producing an alcohol compound, which is characterized by comprising allowing an alcohol in a supercritical state to act on the amide compound or amine compound in the presence of a carboxylic acid derivative to obtain the alcohol compound.

4 Claims, No Drawings

METHOD FOR PRODUCING ALCOHOL COMPOUND

TECHNICAL FIELD

The present invention relates to a method for producing an alcohol compound by which the alcohol compound is produced from an amide compound or amine compound.

BACKGROUND ART

Numerous amide compounds are present in nature, and not a small number thereof can hardly be synthesized by organic synthesis. However, there is a limit to further synthesis development of the amide compounds due to the functional groups and the like that those compounds have. Therefore, it is expected that, when source material compounds capable of being developed by organic synthesis can be produced from these amide compounds, a new way will be paved for synthetic development of pharmaceuticals, intermediate source materials thereof, source materials for chemical products, and the like. Also, amine compounds naturally occur in abundance as amino acids and the like, and it is expected that establishment of a method for converting the functional groups thereof will enlarge the width of synthesis development of pharmaceuticals, intermediate source materials thereof, source materials for chemical products, and the like. For example, it can be considered that alcohol compounds may be obtained from these amide compounds or amine compounds.

As a method for producing an alcohol compound from an amide compound, Patent Literature 1, for example, discloses a method for producing methyl 6-hydroxycaproate by causing methanol in a supercritical state to act on nylon 6. Also, as a method for producing an alcohol compound from an amine compound, Patent Literature 2, for example, discloses a method for producing a fluorine containing benzyl alcohol derivative by causing an acid and alkali nitrite to react with a fluorine-containing benzylamine derivative.

CITATION LIST

Patent Literatures

Patent Literature 1: WO07/088,756
Patent Literature 2: Japanese Patent Application Laid open (JP-A) No 2000-86583

DISCLOSURE OF INVENTION

Problem to be Solved by the Invention

However, the methods disclosed in these Patent Literatures 1 and 2, and others raise a problem in that the yield of the obtained alcohol compound is not sufficient.

Therefore, an object of the present invention is to provide a method for producing an alcohol compound, which enables the alcohol compound to be obtained at a high yield from an amide compound or amine compound.

Means for Solving Problem

In order to achieve the aforementioned object, the present inventors and others have made eager studies and, as a result thereof, found out that an alcohol compound can be obtained at a high yield from an amide compound or amine compound by causing an alcohol in a supercritical state to act on the amide compound or amine compound in the presence of a carboxylic acid derivative. In other words, the present invention is a method for producing an alcohol compound, which is characterized by comprising allowing an alcohol in a supercritical state to act on an amide compound or amine compound in the presence of a carboxylic acid derivative to obtain the alcohol compound.

Effect of the Invention

As described above, according to the present invention, there can be provided a method for producing an alcohol compound, which enables the alcohol compound to be obtained at a high yield from an amide compound or amine compound.

DESCRIPTION OF EMBODIMENTS

In the method for producing an alcohol compound according to the present invention, the amide compound used as a source material includes, for example, an amide compound represented by chemical formula 1. In the formula, $R^1$ is a hydrocarbon group having a carbon number of 1 to 50, preferably having a carbon number of 1 to 36, and specific examples thereof include straight-chain or branched alkyl groups such as methyl, ethyl, n-propyl, i-propyl, n-butyl, i-butyl, n-pentyl, i-pentyl, hexyl, and octyl, and aromatic alkyl groups such as benzyl, preferably octyl or benzyl. $R^2$ is hydrogen or a hydrocarbon group having a carbon number of 1 to 50, preferably having a carbon number of 1 to 36, and specific examples thereof include hydrogen and straight-chain or branched alkyl groups such as methyl and ethyl, preferably hydrogen or methyl. $R^3$ includes, for example, a hydrocarbon group having a carbon number of 1 to 50, preferably having a carbon number of 1 to 36, still more preferably having a carbon number of 1 to 24. Specific examples thereof include: straight-chain or branched alkyl groups such as methyl, ethyl, n-propyl, i-propyl, n-butyl, i-butyl, n-pentyl, i-pentyl, hexyl, octyl, dodecyl, and benzyl; and aromatic alkyl groups such as benzyl, preferably dodecyl, hexyl, or benzyl. Also, $R^1$ and $R^2$ may be bonded to form a ring. The ring to be formed includes, for example, a 3-membered to 50-membered ring, preferably 4-membered to 24-membered ring, and preferably 7-membered ring or 13-membered ring.

$$R^1CONR^2R^3 \qquad \text{[chemical formula 1]}$$

Specific examples of these amide compounds include N-dodecyloctanoic acid amide, N,N-dimethylformamide, N,N-diethylformamide, N,N-di-i-propylformamide, N,N-dibutylformamide, N,N-dipentylformamide, N,N-dioctylformamide, N-methyl, N-stearylformamide, and cyclic amides such as ε-caprolactam, ω-laurolactam, and N-methylcaprolactam, preferably N-dodecyloctanoic acid amide, ε-caprolactam, and ω-laurolactam.

In the method for producing an alcohol compound according to the present invention, when the amide compound represented by chemical formula 1 is used as a source material compound, the bond on the amino group side that forms the amide bond thereof is cut, whereby the amide bond is substituted with a hydroxyl group, and an alcohol compound represented by chemical formula 2 is obtained. For example, when N-dodecyloctanoic acid amide is used as a source material compound, 1-dodecanol can be obtained.

$$R^3OH \qquad \text{[chemical formula 2]}$$

In the method for producing an alcohol compound according to the present invention, the amine compound used as a source material includes, for example, an aliphatic primary amine, aliphatic secondary amine, aliphatic tertiary amine, aromatic amine, diamine compound, cyclic amine compound, or the like.

The aliphatic primary amine, aliphatic secondary amine, aliphatic tertiary amine, and aromatic amine include, for example, a compound represented by chemical formula 3. In the formula, $R^3$ has the same meaning as in chemical formula 1, and $R^4$ and $R^5$ are hydrogen or a hydrocarbon group having a carbon number of 1 to 24, preferably having a carbon number of 1 to 18, still more preferably having a carbon number of 1 to 12, and specific examples thereof include hydrogen, straight-chain or branched alkyl groups such as methyl, ethyl, n-propyl, i-propyl, n-butyl, i-butyl, n-pentyl, i-pentyl, hexyl, and octyl, and aromatic alkyl groups such as benzyl. $R^3$ to $R^5$ may be identical to each other or different from each other.

  [chemical formula 3]

Specific examples of these amine compounds include primary amines such as methylamine, ethylamine, propylamine, butylamine, pentylamine, hexylamine, heptylamine, octylamine, nonylamine, decylamine, undecylamine, dodecylamine, tridecylamine, tetradecylamine, pentadecylamine, cetylamine, and benzylamine, secondary amines such as N-methyldodecylamine, and dibenzylamine, and tertiary amines such as N,N-dimethyldodecylamine and tribenzylamine, preferably dodecylamine, hexylamine, benzylamine, dibenzylamine, or tribenzylamine.

In the method for producing an alcohol compound according to the present invention, when the amine compound represented by chemical formula 3 is used as a source material compound, the amino group thereof is substituted with a hydroxyl group, and an alcohol compound represented by chemical formula 2 is obtained. For example, when dodecylamine is used as a source material compound, 1-dodecanol can be obtained.

The cyclic amide compound includes, for example, a cyclic amine represented by chemical formula 5. In the formula, n is an integer of 2 to 12, more preferably 6 to 12, and the hydrogen bonded to each carbon may be substituted with another functional group unless the functional group inhibits the reaction in the method for producing an alcohol compound according to the present invention.

  [chemical formula 5]

Specific examples of these cyclic amine compounds include hexamethyleneimine, heptamethyleneimine, octamethyleneimine, and dodecamethyleneimine, preferably hexamethyleneimine, heptamethyleneimine, octamethyleneimine, or dodecamethyleneimine.

The diamine compound includes, for example, a diamine represented by chemical formula 7. In the formula, n is an integer of 2 to 12, more preferably 6 to 12, and the hydrogen bonded to each carbon may be substituted with another functional group unless the functional group inhibits the reaction in the method for producing an alcohol compound according to the present invention.

  [chemical formula 7]

Specific examples of these diamine compounds include hexamethylenediamine and dodecamethylenediamine, preferably hexamethylenediamine.

In the method for producing an alcohol compound according to the present invention, when the cyclic amine compound represented by chemical formula 5 or the diamine compound represented by chemical formula 7 is used as a source material compound, the amino group thereof is substituted with a hydroxyl group, and a dial represented by chemical formula 6 is obtained. For example, when hexamethyleneimine or hexamethylenediamine is used as a source material compound, 1,6-hexanediol can be obtained.

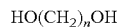  [chemical formula 6]

The method for producing an alcohol compound according to the present invention is a novel method for producing the alcohol compound from an amide compound or amine compound, and then a new way can be paved for synthetic development of pharmaceuticals, intermediate source materials, and source materials for chemical products, for example.

Examples of the alcohol used in the method for producing an alcohol compound according to the present invention include methanol, ethanol, 1-propanol (n-propanol), 2-propanol (isopropanol), allyl alcohol, 1-butanol (n-butanol), 2-butanol (sec-butanol), 2-methyl-1-propanol (isobutanol), 2-methyl-2-propanol (t-butanol) 3-butene-2-ol, crotyl alcohol, cyclopropanemethanol, 3-butene-1-ol, 2-methyl-2-propene-1-ol, 3-butyne-1-ol, 2-butyne-1-ol, 3-butyne-2-ol, 1-pentanol (n-pentanol), 2-pentanol (sec-amyl alcohol), 3-pentanol, 2-methyl-1-butanol, 2-methyl-2-butanol, 3-methyl-2-butanol, 3-methyl-1-butanol, 2,2-dimethyl-1-propanol (t-amyl alcohol), 1-cyclopropylethanol, 1-pentene-3-ol, 4-pentene-2-ol, 4-pentene-1-ol, 3-pentene-2-ol, 3-methyl-3-butene-1-ol, 2-methyl-3-butene-2-ol, 3-methyl-2-butene-1-ol, cyclobutanemethanol, 2-methylcyclopropanemethanol, 2-methyl-3-butene-1-ol, 2-methyl-3-butyne-2-ol, 2-pentyne-1-ol, 4-pentyne-2-ol, 4-pentyne-1-ol, 1,4-pentadiene-3-ol, 2-pentyne-1-ol, 1-hexanol (n-hexanol), 2-hexanol, 3-hexanol, 3-methyl-3-pentanol, 4-methyl-1-pentanol, 4-methyl-2-pentanol, 3-methyl-1-pentanol, 2-methyl-2-pentanol, 3-methyl-2-pentanol, 2-methyl-3-pentanol, 2-methyl-1-pentanol, 2-ethyl-1-butanol, 2,3-dimethyl-2-butanol, 3,3-dimethyl-2-butanol, 3,3-dimethyl-1-butanol, cyclohexanol, 1-heptanol (n-heptanol), 2-heptanol, 3-heptanol, 2-methyl-3-hexanol, 2-methyl-2-hexanol, 5-methyl-1-hexanol, 5-methyl-1-hexanol, 2,2-dimethyl-3-pentanol, 3-ethyl-3-pentanol, 2,3-dimethyl-3-pentanol, 2,4-dimethyl-3-pentanol, 4,4-dimethyl-2-pentanol, 1-octanol (n-octanol), 2-octanol, 3-octanol, 6-methyl-2-heptanol, 4-methyl-3-heptanol, 2-ethyl-1-hexanol, 2,4,4-trimethyl-1-pentanol, 2-propyl-1-pentanol, 1-nonanol, 2-nonanol, 3-methyl-3-octanol, 2,6-dimethyl-4-heptanol, 3,5,5-trimethyl-1-hexanol, 3-ethyl-2,2-dimethyl-3-pentanol, 1-decanol (n-decanol), 2-decanol, 3,7-dimethyl-1-octanol, 3,7-dimethyl-3-octanol, 1-undecanol, 2-undecanol, 1-dodecanol (n-dodecanol), 2-dodecanol, 2-butyl-1-octanol, cyclododecanol, 1-tridecanol, 1-tetradecanol, 2-tetradecanol, 1-pentadecanol, 1-hexadecanol, 2-hexadecanol, 2-hexyl-1-decanol, 1-heptadecanol, and 1-octadecanol. The carbon number of these alcohols is not particularly limited; however, a primary alcohol is preferable; a chain-form aliphatic alcohol having a carbon number of 1 to 6 such as methanol, ethanol, n-propanol, n-butanol, n-pentanol, or n-hexanol is more preferable; and particularly methanol is preferable.

These alcohols can be brought into a supercritical state, for example, by heating and pressurizing these alcohols or by heating the alcohols in a tightly closed state. The critical temperature and critical pressure of principal alcohols are as shown in Table 1.

TABLE 1

|  | Critical temperature (° C.) | Critical pressure (MPaG) |
|---|---|---|
| Methanol | 239 | 8.1 |
| Ethanol | 243 | 6.4 |
| n-Propanol | 264 | 5.2 |
| n-Butanol | 290 | 4.4 |

When the alcohols are allowed to act in a state close to the supercritical state, the reaction temperature is, for example, 200 to 400° C., preferably 220 to 330° C., more preferably 250° C. or higher. Also, the pressure is 5 to 40 MPaG (G represents a gauge pressure), preferably 8 MPaG or higher.

In the method for producing an alcohol compound according to the present invention, the amide compound or amine compound, the alcohol, and the carboxylic acid derivative may be simultaneously mixed and thereafter the alcohol may be brought into a supercritical state by heating or the like, or alternatively, the alcohol and the carboxylic acid derivative may be mixed and brought into a supercritical state and thereafter the resultant may be added to the amide compound or amine compound.

In the method for producing an alcohol compound according to the present invention, the reaction time for allowing the amide compound or amine compound and the alcohol to react is preferably 5 minutes to 48 hours, more preferably 0.5 hour to 24 hours, still more preferably 1 hour to 6 hours.

The ratio of the amide compound or amine compound relative to the total amount of the alcohol that is allowed to act thereon is preferably more than 0 and 50 wt % or less, more preferably 0.5 to 30 wt %, still more preferably 3 to 10 wt %.

The carboxylic acid derivative used in the method for producing an alcohol compound according to the present invention is not particularly limited; however, a carboxylic acid, a carboxylic acid ester, or the like is preferable.

The carboxylic acid includes, for example, aliphatic carboxylic acid or aromatic carboxylic acid.

The aliphatic carboxylic acid includes an aliphatic carboxylic acid having a carbon number of 1 to 12, preferably an aliphatic carboxylic acid having a carbon number of 2 to 8. Specific examples thereof include acetic acid, propionic acid, butyric acid, methoxyacetic acid, pentanoic acid, caproic acid, heptanoic acid, octanoic acid, lactic acid, glycolic acid, and the like, preferably acetic acid, lactic acid, glycolic acid, or octanoic acid.

Examples of the aromatic carboxylic acid include terephthalic acid, isophthalic acid, orthophthalic acid, trimellitic acid, benzoic acid, cresolic acid, naphthoic acid, naphthalenedicarboxylic acid, and the like, preferably benzoic acid.

The carboxylic acid ester includes, for example, an ester of the aforementioned aliphatic carboxylic acid or aromatic carboxylic acid and the ester with a straight chain or branched alkyl alcohol having a carbon number of 1 to 50, preferably having a carbon number of 1 to 36, still more preferably having a carbon number of 1 to 24. Specific examples thereof include methyl acetate, methyl glycolate, methyl propionate, and the like.

The amount of use of the carboxylic acid derivative is preferably 1 to 1000 wt %, more preferably 71 to 1270 wt %, relative to the amide compound or amine compound. Here, when the amount of use of the carboxylic acid derivative is small, the reaction speed may decrease or the yield of the hydroxycarboxylic acid derivative may decrease.

A reaction apparatus used in the present invention includes, for example, a tubular tank equipped with a stirring apparatus, a pipe-type reaction tube, or the like. A reaction method includes either of the continuous method and the batch method. The amide compound or amine compound, the carboxylic acid derivative, and the alcohol can be separately supplied into the reaction apparatus, or alternatively, a mixture obtained by mixing these in advance may be supplied into the reaction apparatus. From a reaction liquid containing the alcohol compound obtained by the method for producing an alcohol compound according to present invention, the alcohol and the carboxylic acid derivative that have been allowed to act on the amide compound or amine compound are separated and removed by flash distillation or the like. When it is desired that an alcohol compound having a high purity is obtained, the resultant is further refined by reduced-pressure distillation or the like.

EXAMPLES

Next, Examples of the method for producing an alcohol compound according to the present invention will be described; however, the present invention is not limited by these Examples, so that change can be made within a range that does not depart from the gist of the present invention.

In the Examples, a reactor constituted of a stainless steel (SUS316) pipe (outer diameter of ⅜ inch, inner diameter of 7.53 mm, length of 23 cm) and a two-end cap (SS-600-C manufactured by Swagelok Co., Ltd.) and having a volume of 10 mL was prepared and used. In order to heat up to the reaction temperature, an electric furnace (DRD360DA manufactured by ADVANTEC Co., Ltd.) was used. For gas chromatography measurement, GC-2014 manufactured by Shimadzu Corporation was used. The yield of the produced object alcohol was calculated on the basis of [mol amount of produced object alcohol]/[mol amount of introduced amide compound or amine compound]×100.

Reference Example 1

Method for Synthesizing N-Dodecyloctanoic Acid Amide

Into a 500 mL two-neck flask, dodecylamine (18.69 g) and DMAP (N,N-dimethyl-4-aminopyridine) (3.67) were added and nitrogen substitution was carried out. Subsequently, dichloromethane (150 mL) and potassium carbonate (16.67 g) were added to this. In a state in which this flask was cooled in an ice bath, a solution obtained by mixing dichloromethane (150 mL) and octanoic acid chloride (17.94 g) was dropwise added. After the dropwise addition was finished, the temperature was raised to room temperature, and the reaction was carried out for 4 hours. The end of the reaction was confirmed by gas chromatography, and 50 mL of saturated aqueous solution of ammonium chloride was added. After the resultant was stirred for 10 minutes, extraction was carried out with dichloromethane (100 mL), and the obtained organic phase was washed with 1M aqueous solution of hydrochloric acid (50 mL), saturated aqueous solution of sodium hydrogencarbonate (50 mL), and saturated aqueous solution of sodium chloride (50 mL). Removal of the solvent by reduced-pressure distillation was carried out using an evaporator, and recrystallization was carried out with dichloromethane-hexane. The yield of the object N-dodecyloctanoic acid amide was 89% (20.13 g, 89.42 mmol) in terms of dodecylamine.

Example 1

Into a pipe reactor having a volume of 10 mL, N-dodecyloctanoic acid amide (0.30 g), methanol (4.00 g), and methyl octanoate (0.64 g) as a carboxylic acid derivative were added, and the reactor was tightly closed after nitrogen substitution at room temperature. The reactor was put into an electric furnace heated to 330° C., and reaction was carried out for 3 hours (pressure of 34.0 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and cyclododecanol as an internal standard substance were weighed as an analysis sample for gas chromatography analysis. An integrated value was calculated by gas chromatography analysis, and the yield was determined from a prepared calibration line table. As a result thereof, the yield of 1-dodecanol was 62%.

Example 2

The reaction was carried out (pressure of 33.0 MPa) in the same manner as in Example 1 except that the carboxylic acid derivative was changed to methyl acetate (0.38 g). As a result thereof, the yield of 1-dodecanol was 57%.

Example 3

The reaction was carried out (pressure of 33.0 MPa) in the same manner as in Example 1 except that the carboxylic acid derivative was changed to methyl propionate (0.45 g). As a result thereof, the yield 1-dodecanol was 62%.

Example 4

The reaction was carried out (pressure of 33.1 MPa) in the same manner as in Example 1 except that the carboxylic acid derivative was changed to lactic acid (0.46 g). As a result thereof, the yield of 1-dodecanol was 66%.

Example 5

The reaction was carried out (pressure of 34.0 MPa) in the same manner as in Example 1 except that the carboxylic acid derivative was changed to benzoic acid (0.62 g). As a result thereof, the yield of 1-dodecanol was 67%.

Example 6

The reaction was carried out (pressure of 32.8 MPa) in the same manner as in Example 8 except that the carboxylic acid derivative was changed to glycolic acid (0.38 g). As a result thereof, the yield of 1-dodecanol was 67%.

Comparative Example 1

The reaction was carried out (pressure of 28.0 MPa) in the same manner as in Example 6 except that the carboxylic acid derivative was not added. As a result thereof, the yield of 1-dodecanol was 19%.

Example 7

Into a pipe reactor (outer diameter of ⅜ inch, inner diameter of 7.53 min, length of 23 cm) having a volume of 10 ml, N-dodecyloctanoic acid amide (0.30 g), methanol (3.00 g), and acetic acid (0.60 g) were added, and the reactor was tightly closed after nitrogen substitution at room temperature. The reactor was put into an electric furnace heated to 330° C., and reaction was carried out for 3 hours (pressure of 24.0 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and cyclododecanol as an internal standard substance were weighed as an analysis sample for gas chromatography analysis. An integrated value was calculated by gas chromatography analysis, and the yield was determined from a prepared calibration line table. As a result thereof, the yield of 1-dodecanol was 67%.

Example 8

Into a pipe reactor having a volume of 10 mL, dodecyloctanoic acid amide (0.30 g), methanol (3.01 g), and methyl acetate (0.76 g) were added, and the reactor was tightly closed after nitrogen substitution at room temperature. The reactor was put into an electric furnace heated to 330° C., and reaction was carried out for 3 hours (pressure of 24.4 MPa). Thereafter, the reactor was taken out from the electric furnace and quickly cooled by cold-water bath to stop the reaction. Aft confirming that the reactor had been sufficiently cooled, the reaction mixture was taken out with methanol and collected. The obtained reaction mixture and cyclododecanol as an internal standard substance were weighed as an analysis sample for gas chromatography analysis. An integrated value was calculated by gas chromatography analysis, and the yield was determined from a prepared calibration line table. As a result thereof, the yield of 1-dodecanol was 64%.

Example 9

Into a pipe reactor having a volume of 10 mL, N-dodecyloctanoic acid amide (0.30 g), methanol (3.01 g), and lactic acid (0.46 g) were added, and the reactor was tightly closed after nitrogen substitution at room temperature. The reactor was put into an electric furnace heated to 300° C., and reaction was carried out for 3 hours (pressure of 18.0 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and cyclododecanol as an internal standard substance were weighed as an analysis sample for gas chromatography analysis. An integrated value was calculated by gas chromatography analysis, and the yield was determined from a prepared calibration line table. As a result thereof, the yield of 1-dodecanol was 57%.

Example 10

Into a pipe reactor having a volume of 10 mL, N-dodecyloctanoic acid amide (0.3 g), acetic acid (0.30 g), and methanol (3.0 g) were added, and the reactor was tightly closed after nitrogen substitution at room temperature. The reactor was put into an electric furnace heated to 300° C. (pressure of 17.8 MPa), and change with lapse of time was measured. For measurement, the obtained reaction mixture and cyclododecanol as an internal standard substance were weighed as an analysis sample for gas chromatography analysis. An integrated value was calculated by gas chromatography analysis, and the yield of 1-dodecanol was determined from a prepared calibration line table. A result of these is shown in Table 2.

TABLE 2

| Temperature (° C.) | Reaction time (min) | Yield (%) |
|---|---|---|
| 300 | 120 | 61 |
|  | 140 | 66 |
|  | 160 | 69 |
|  | 180 | 68 |
|  | 240 | 71 |
|  | 300 | 70 |
|  | 360 | 69 |

Example 11

Into a pipe reactor having a volume of 10 mL, dodecylamine (0.19 g), octanoic acid (0.14 g) as a carboxylic acid derivative, and methanol (4.0 g) were added, and the reactor was tightly closed after nitrogen substitution at room temperature. The reactor was put into an electric furnace heated to 330° C., and reaction was carried out for 4 hours (pressure of 28.1 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and cyclododecanol as an internal standard substance were weighed as an analysis sample for gas chromatography analysis. An integrated value was calculated by gas chromatography analysis, and the yield was determined from a prepared calibration line table. As a result thereof, the yield of 1-dodecanol was 53%.

Comparative Example 2

The reaction was carried out (pressure of 26.2 MPa) in the same manner as in Example 11 except that the carboxylic acid derivative was not added. As a result thereof, the yield of 1-dodecanol was 4%.

Example 12

Into a pipe reactor having a volume of 10 mL, benzylamine (0.10 g), methanol (3.02 g), and glycolic acid (0.38 g) were added, and the reactor was tightly closed after nitrogen substitution at room temperature. The reactor was put into an electric furnace heated to 270° C., and reaction was carried out for 160 minutes (pressure of 10.7 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and hexanol as an internal standard substance were weighed as an analysis sample for gas chromatography analysis. An integrated value was calculated by gas chromatography analysis, and the yield was determined from a prepared calibration line table. As a result thereof, the yield of benzyl alcohol was 72%.

Example 13

The reaction was carried out (pressure of 14.5 MPa) in the same manner as in Example 12 except that the reaction temperature was set to be 300° C. and the reaction time was set to be 120 minutes. As a result thereof, the yield of benzyl alcohol was 71%.

Example 14

The reaction was carried out (pressure of 10.8 MPa) in the same manner as in Example 12 except that the amount of addition of glycolic acid was set to be 0.071 g and the reaction time was set to be 360 minutes. As a result thereof, the yield of benzyl alcohol was 77%.

Example 15

The reaction was carried out (pressure of 10.7 MPa) in the same manner as in Example 14 except that acetic acid (1.27 g) was used as the carboxylic acid derivative. As a result thereof, the yield of benzyl alcohol was 65%.

Comparative Example 3

The reaction was carried out (pressure of 10.6 MPa) in the same manner as in Example 14 except that the carboxylic acid derivative was not added. As a result thereof, the yield of benzyl alcohol was 3%.

Example 16

Into a pipe reactor having a volume of 10 dibenzylamine (0.10 g), methanol (3.00 g), and glycolic acid (0.38 g) were added, and the reactor was tightly closed after nitrogen substitution at room temperature. The reactor was put into an electric furnace heated to 300° C., and reaction was carried out for one hour (pressure of 14.5 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and hexanol as an internal standard substance were weighed as an analysis sample for gas chromatography analysis. An integrated value was calculated by gas chromatography analysis, and the yield was determined from a prepared calibration line table. As a result thereof, the yield of benzyl alcohol was 83%.

Comparative Example 4

The reaction was carried out (pressure of 14.5 MPa) in the same manner as in Example 16 except that the carboxylic acid derivative was not added. As a result thereof, the yield of benzyl alcohol was 20%.

Example 17

Into a pipe reactor having a volume of 10 tribenzylamine (0.10 g), methanol (3.01 g), and glycolic acid (0.38 g) were added, and the reactor was tightly closed after nitrogen substitution at room temperature. The reactor was put into an electric furnace heated to 270° C., and reaction was carried out for 6 hours (pressure of 10.7 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and hexanol as an internal standard substance were weighed as an analysis sample for gas chromatography analysis. An integrated value was calculated by gas chromatography analysis, and the yield was determined from a prepared calibration line table. As a result thereof, the yield of benzyl alcohol was 33%.

Example 18

Into a pipe reactor having a volume of 10 mL, hexamethyleneimine (0.11 g), methanol (3.01 g), and glycolic acid (0.23 g) were added, and the reactor was tightly closed after nitrogen substitution at room temperature. The reactor was put into an electric furnace heated to 250° C., and reaction was carried out for 6 hours (pressure of 8.8 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a prepared calibration line table. As a result thereof, the yield of 1,6-hexanediol was 42%.

Example 19

The reaction was carried out (pressure of 8.9 MPa) in the same manner as in Example 18 except that the amount of addition of glycolic acid was set to be 0.77 g. As a result thereof, the yield of 1,6-hexanediol was 41%.

Example 20

The reaction was carried out (pressure of 10.8 MPa) in the same manner as in Example 19 except that the reaction temperature was set to be 270° C. and the reaction time was set to be 100 minutes. As a result thereof, the yield of 1,6-hexanediol was 37%.

Example 21

The reaction was carried out (pressure of 14.7 MPa) in the same manner as in Example 19 except that the reaction temperature was set to be 300° C. and the reaction time was set to be one hour. As a result thereof, the yield of 1,6-hexan dial was 36%.

Example 22

The reaction was carried out (pressure of 8.6 MPa) in the same manner as in Example 18 except that lactic acid (1.14 g) was used as the carboxylic acid derivative. As a result thereof, the yield of 1,6-hexanediol was 38%.

Example 23

The reaction was carried out (pressure of 8.6 MPa) in the same manner as in Example 18 except that benzoic acid (1.23 g) was used as the carboxylic acid derivative. As a result thereof, the yield of 1,6-hexanediol was 31%.

Example 24

Into a pipe reactor having a volume of 10 mL, heptamethyleneimine (0.10 g), methanol (3.00 g), and glycolic acid (0.20 g) were added, and the reactor was tightly closed after nitrogen substitution at room temperature. The reactor was put into an electric furnace heated to 300° C., and reaction was carried out for 140 minutes (pressure of 14.5 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and benzyl alcohol as an internal standard substance were weighed as an analysis sample for gas chromatography analysis. An integrated value was calculated by gas chromatography analysis, and the yield was determined from a prepared calibration line table. As a result thereof, the yield of 1,7-heptanediol was 61%.

Example 25

The reaction was carried out (pressure of 8.6 MPa) in the same manner as in Example 25 except that the reaction temperature was set to be 250° C. and the reaction time was set to be 240 minutes. As a result thereof, the yield of 1,7-heptanediol was 48%.

Example 26

The reaction was carried out (pressure of 10.7 MPa) in the same manner as in Example 25 except that the reaction temperature was set to be 270° C. and the reaction time was set to be 360 minutes. As a result thereof, the yield of 1,7-heptanediol was 52%.

Example 27

Into a pipe reactor having a volume of 10 mL, octamethyleneimine (0.10 g), methanol (3.00 g), and glycolic acid (0.18 g) were added, and the reactor was tightly closed after nitrogen substitution at room temperature. The reactor was put into an electric furnace heated to 300° C., and reaction was carried out for 4 hours (pressure of 14.5 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a prepared calibration line table. As a result thereof, the yield of 1,8-octanediol was 54%.

Example 28

The reaction was carried out (pressure of 8.7 MPa) in the same manner as in Example 28 except that the reaction temperature was set to be 250° C. and the reaction time was set to be 360 minutes. As a result thereof, the yield of 1,8-octanediol was 52%.

Example 29

The reaction was carried out (pressure of 10.7 MPa) in the same manner as in Example 28 except that the reaction temperature was set to be 270° C. and the reaction time was set to be 300 minutes. As a result thereof, the yield of 1,8-octanediol was 54%.

Example 30

Into a pipe reactor having a volume of 10 mL, dodecamethyleneimine (0.10 g), methanol (3.00 g), and glycolic acid (0.12 g) were added, and the reactor was tightly closed after nitrogen substitution at room temperature. The reactor was put into an electric furnace heated to 300° C., and reaction was carried out for 240 minutes (pressure of 14.5 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a prepared calibration line table. As a result thereof, the yield of 1,12-dodecanediol was 56%.

Example 31

Into a pipe reactor having a volume of 10 mL, 1,6-hexanediamine (0.10 g), methanol (3.00 g), and glycolic acid (0.20 g) were added, and the reactor was tightly closed after nitrogen substitution at room temperature. The reactor was put into an electric furnace heated to 270° C., and reaction was carried out for 160 minutes (pressure of 10.6 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a prepared calibration line table. As a result thereof, the yield of 1,6-hexanediol was 43%.

Example 32

Into a pipe reactor having a volume of 10 mL, ε-caprolactam (0.10 g), methanol (3.00 g), and glycolic acid (0.23 g) were added, and the reactor was tightly closed after nitrogen substitution at room temperature. The reactor was put into an electric furnace heated to 300° C., and reaction was carried out for 180 minutes (pressure of 14.6 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a prepared calibration line table. As a result thereof, the yield of methyl hydroxyhexanoate was 41.2%.

Example 33

Into a pipe reactor having a volume of 10 mL, ω-laurolactam (0.10 g), methanol (3.00 g), and glycolic acid (0.23 g) were added, and the reactor was tightly closed after nitrogen substitution at room temperature. The reactor was put into an electric furnace heated to 300° C., and reaction was carried out for 240 minutes (pressure of 14.6 MPa). Thereafter, the reactor was taken out from the electric furnace and quickly cooled by cold-water bath to stop the reaction. After confirming that the reactor had been sufficiently cooled, the reaction mixture was taken out with methanol and collected. The obtained reaction mixture and anisole as an internal standard substance were weighed as an analysis sample for gas chromatography analysis. An integrated value was calculated by gas chromatography analysis, and the yield was determined from a calibration line table prepared by using, as a factor of methyl hydroxydodecanoate, that of ω-laurolactam. As a result thereof, the yield of methyl hydroxydodecanoate was 67.7%.

The invention claimed is:

1. A method for producing an alcohol compound, comprising allowing an alcohol in a supercritical state to react with an amide compound represented by chemical formula 1 in the presence of a carboxylic acid or ester thereof to form the alcohol compound represented by chemical formula 2, $$R^1CONR^2R^3 \quad \text{[chemical formula 1]}$$

wherein in the formula, $R^1$ is a hydrocarbon group having a carbon number of 1 to 50; $R^2$ is hydrogen or a hydrocarbon group having a carbon number of 1 to 50; $R^3$ is a hydrocarbon group having a carbon number of 1 to 50; and $R^1$ and $R^2$ may be bonded to form a ring; and $$R^3OH \quad \text{[chemical formula 2]}$$

wherein in the formula, $R^3$ is the same as that of chemical formula 1.

2. A method for producing an alcohol compound, comprising allowing an alcohol in a upercritical state to react with an amine compound represented by chemical formula 3 in the presence of a carboxylic acid or ester thereof to form the alcohol compound represented by chemical formula 4, $$R^3R^4R^5N \quad \text{[chemical formula 3]}$$

wherein in the formula, $R^3$ is a hydrocarbon group having a carbon number of 1 to 50, $R^4$ and $R^5$ are hydrogen or a hydrocarbon group having a carbon number of 1 to 24, and $R^3$ to $R^5$ may be identical to each other or different from each other; and $$R^3OH \quad \text{[chemical formula 4]}$$

wherein in the formula, $R^3$ is the same as that of chemical formula 3.

3. A method for producing an alcohol compound, comprising allowing an alcohol in a supercritical state to react with a cyclic amine compound represented by chemical formula 5 in the presence of a carboxylic acid or ester thereof to form the alcohol compound represented by chemical formula 6,

[chemical formula 5]

wherein in the formula, n is an integer from 2 to 12; and the hydrogen bonded to each carbon may be substituted with another functional group; and $$HO(CH_2)_nOH \quad \text{[chemical formula 6]}$$

wherein in the formula, n is an integer from 2 to 12; and the hydrogen bonded to each carbon may be substituted with another functional group.

4. A method for producing an alcohol compound, comprising allowing an alcohol in a supercritical state to react with a diamine compound represented by chemical formula 7 in the presence of a carboxylic acid or ester thereof to form the alcohol compound represented by chemical formula 8, $$NH(CH_2)_nNH \quad \text{[chemical formula 7]}$$

wherein in the formula, n is an integer from 2 to 12; and the hydrogen bonded to each carbon may be substituted with another functional group; and HO(CH$_2$)$_n$OH   [chemical formula 8]

wherein in the formula, n is an integer from 2 to 12; and the hydrogen bonded to each carbon may be substituted with another functional group.

* * * * *